(12) United States Patent  (10) Patent No.: US 6,583,727 B2
Nunome  (45) Date of Patent: Jun. 24, 2003

(54) PATIENT DETECTING APPARATUS

(75) Inventor: Tomohiro Nunome, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/028,706

(22) Filed: Dec. 28, 2001

(65) Prior Publication Data

US 2002/0196148 A1 Dec. 26, 2002

(30) Foreign Application Priority Data

Jun. 25, 2001 (JP) ........................................ 2001-191595

(51) Int. Cl.[7] .............................................. G08B 21/00
(52) U.S. Cl. ................ 340/665; 340/573.1; 340/573.4; 340/666; 340/286.07
(58) Field of Search ................................ 340/665, 666, 340/667, 286.07, 575, 573.4, 573.1; 601/150, 148; 200/85 R; 5/713, 714

(56) References Cited

U.S. PATENT DOCUMENTS

| | | | | |
|---|---|---|---|---|
| 3,653,083 A | * | 4/1972 | Lapidus | 5/348 |
| 4,020,482 A | * | 4/1977 | Feldl | 340/666 |
| 4,280,487 A | * | 7/1981 | Jackson | 128/33 |
| 5,184,112 A | * | 2/1993 | Gusakov | 340/573 |

* cited by examiner

Primary Examiner—Anh La
(74) Attorney, Agent, or Firm—Oliff & Berridge PLC (57) ABSTRACT

An apparatus for detecting a patient, including a plurality of pressure detecting devices which are adapted to be placed on a bed such that the pressure detecting devices are arranged in a widthwise direction of the bed, and which detect respective pressures and produce respective pressure signals representing the detected pressures, and a position detecting device for detecting, based on the pressure signals supplied from the pressure detecting devices, a position, in the widthwise direction of the bed, where the patient is present.

2 Claims, 5 Drawing Sheets

PATIENT DETECTING APPARATUS

BACKGROUND OF THE INVENTION

1. Field of the Invention

The present invention relates to a patient detecting apparatus which detects that a patient is present on a bed and particularly to such a patient detecting apparatus which can detect a position on a bed where a patient is present.

2. Related Art Statement

If an inpatient who is sleeping on a bed accidentally falls off the bed, the patient may be injured. However, if the patient cannot move without help, the patient cannot inform a doctor or a nurse of his or her injury, so that treatment of the injury may be delayed. To avoid this, there has conventionally been used a patient detecting apparatus which detects whether a patient is present on a bed. In addition, the patient detecting apparatus may be used to detect whether a poriomaniac patient is absent from a bed.

The conventional patient detecting apparatus includes a pressure detecting device which is placed on a particular portion of a bed on which a patient sleeps and, when the pressure detecting device detects a pressure higher than a predetermined value, the patient detecting apparatus judges that the patient is present on the bed.

However, the conventional patient detecting apparatus can only judge whether a patient is present on a bed but cannot prevent the patient from falling off the bed.

SUMMARY OF THE INVENTION

It is therefore an object of the present invention to provide a patient detecting apparatus which can detect a position on a bed where a patient is present, in particular, a position where the patient is likely to fall off the bed.

The above object has been achieved by the present invention. According to a first feature of the present invention, there is provided an apparatus for detecting a patient, comprising a plurality of pressure detecting devices which are adapted to be placed on a bed such that the pressure detecting devices are arranged in a widthwise direction of the bed, and which detect respective pressures and produces respective pressure signals representing the detected pressures; and a position detecting means for detecting, based on the pressure signals supplied from the pressure detecting devices, a position, in the widthwise direction of the bed, where the patient is present.

According to this feature, the plurality of pressure detecting devices are placed on the bed such that the pressure detecting devices are arranged in a widthwise direction of the bed, and produce respective pressure signals representing respective detected pressures. Thus, the plurality of pressure signals are obtained in the widthwise direction of the bed. And, the position detecting means detects, based on those pressure signals supplied from the pressure detecting devices, a position, in the widthwise direction of the bed, where the patient is present. Thus, the present apparatus can judge whether the patient is present at a dangerous position where the patient is likely to fall off the bed.

According to a second feature of the present invention, the pressure detecting devices comprise respective bags each of which is filled with a fluid, and the apparatus further comprises a fluid-amount control means for controlling an amount of the fluid present in each of the respective bags of the pressure detecting devices, the fluid-amount control means comprising changing means for identifying a first bag of the respective bags that supports a greatest portion of a total weight of the patient, and changing the respective amounts of the fluid present in the respective bags of two or more pressure detecting devices so that a second bag of the respective bags that is different from the first bag supports a greatest portion of the total weight of the patient.

The bags as the pressure detecting devices are provided at such positions where the bags can always contact the patient so as to detect the position of the patient. Thus, a portion of the patient that is pressed by the bag or bags is likely to suffer bedsores. This problem can be effectively solved according to this feature. That is, the changing means identifies a first bag that supports a greatest portion of a total weight of the patient, and changes the respective amounts of the fluid present in the respective bags of two or more pressure detecting devices so that a second bag different from the first bag supports a greatest portion of the total weight of the patient. Thus, the present apparatus can effectively prevent the patient from suffering bedsores.

According to a third feature of the present invention, the pressure detecting devices comprise respective bags each of which is filled with an air and includes a contact portion that is adapted to contact the patient and is formed of a porous sheet, the porous sheet allowing the air to permeate therethrough into an outside space, and wherein the apparatus further comprises an air pump which supplies the air to said each of the respective bags.

According to this feature, when the air pump supplies the air to each of the bags, the air leaks, little by little, through the porous sheet providing the contact portion of the each bag that contacts the patient. Thus, the present apparatus can effectively prevent portions of the patient that contact the bags, from perspiring on the bags.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
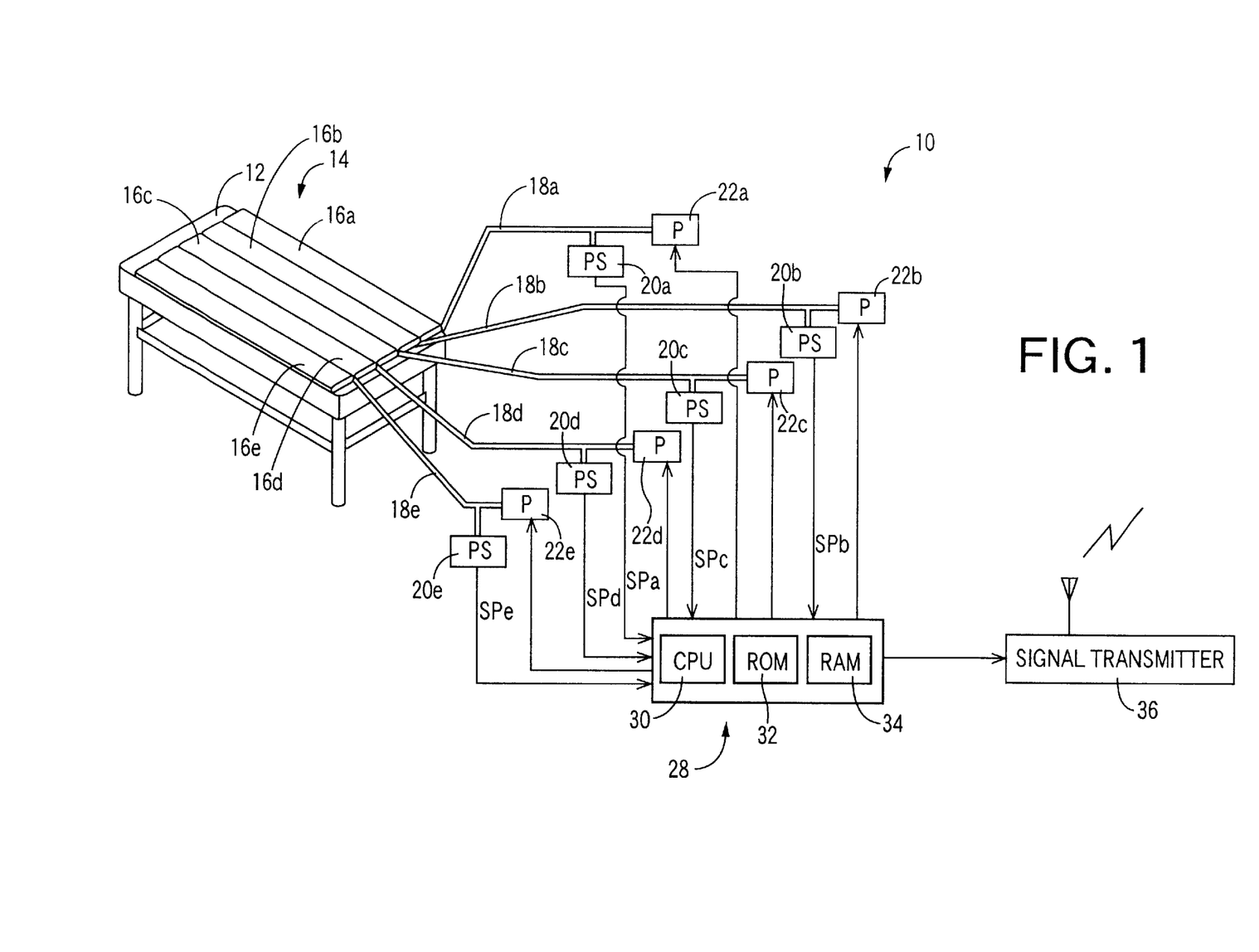
FIG. 1 is a diagrammatic view for explaining a construction of a patient detecting apparatus to which the present invention is applied.

Hereinafter, there will be described an embodiment of the present invention in detail by reference to the drawings. FIG. 1 is a diagrammatic view for explaining a construction of a patient detecting apparatus 10 to which the present invention is applied.

The patient detecting apparatus 10 includes a pressure detecting unit 14 which is adapted to be placed on a bed 12. The pressure detecting unit 14 includes five pressure detecting bags 16a, 16b, 16c, 16d, 16e (hereinafter, referred to as the "pressure detecting bags 16" when it is not needed to distinguish those bags from one another) that are connected to one another in a widthwise direction of the bed 12. The unit 14 as a whole has a widthwise dimension substantially equal to a width of the bed 12. Each of the pressure detecting bags 16 is formed of a non-stretchable sheet that does not allow air to permeate therethrough, and each bag 16 is elongate, flat, and flexible. Each bag 16 has a lengthwise dimension slightly shorter than that of the bed 12, and a thickness of each bag 16 at the time when a pressure of air present therein is equal to a prescribed initial pressure, is equal to, e.g., from several centimeters to five centimeters. Though the pressure detecting unit 14 includes the five pressure detecting bags 16, the unit 14 may include a greater number of pressure detecting bags 16.

The five pressure detecting bags 16 do not communicate with one another, and are connected via respective tubes 18a, 18b, 18c, 18d, 18e to respective pressure sensors 20a, 20b, 20c, 20d, 20e and respective positive displacement pumps 22a, 22b, 22c, 22d, 22e (hereinafter, referred as the "tubes 18", the "pressure sensors 20", and the "positive displacement pumps 22", when it is not needed to distinguish those tubes from one another, those sensors from one another, or those pumps from one another).

The pressure sensors 20 detect, through the respective tubes 18, respective air pressures in the respective pressure detecting bags 16, i.e., respective bag pressures, and supply respective electric signals SP representing the detected bag pressures, to a control device 28. In other words, the pressure sensors 20 convert the respective air pressures in the respective pressure detecting bags 16, to the respective electric signals SP, and supply those electric signals SP to the control device 28.

The positive displacement pumps 22, functioning as a fluid-amount control device, supply or discharge respective amounts of air that are proportional to respective amounts of operation thereof, to or from the respective tubes 18. The pumps 22 may be either of a rotary type or of a reciprocal type. The pumps 22 control the respective amounts of air present in the respective pressure detecting bags 16, and thereby control the respective air pressures in the respective bags 16.

The control device 28 is provided by a so-called microcomputer including a CPU (central processing unit) 30, a ROM (read only memory) 32, a RAM (random access memory) 34, and an I/O (input and output) port, not shown. The CPU 30 processes various signals, according to control programs pre-stored in the ROM 32, while utilizing a temporary-storage function of the RAM 34, and outputs drive or control signals via the I/O port to the displacement pumps 22. In addition, the CPU 30 judges, based on the electric signals SP supplied from the pressure sensors 20, whether a patient is present on the bed 12, and detects a position on the bed 12 where the patient is present. If the patient is not present on the bed 12, or if the patient is present at a dangerous position on the bed 12, the CPU 30 operates a signal transmitter 36 to transmit, toward a signal receiver, not shown, provided at a nurse center, a signal representing each situation.

Figure 2:
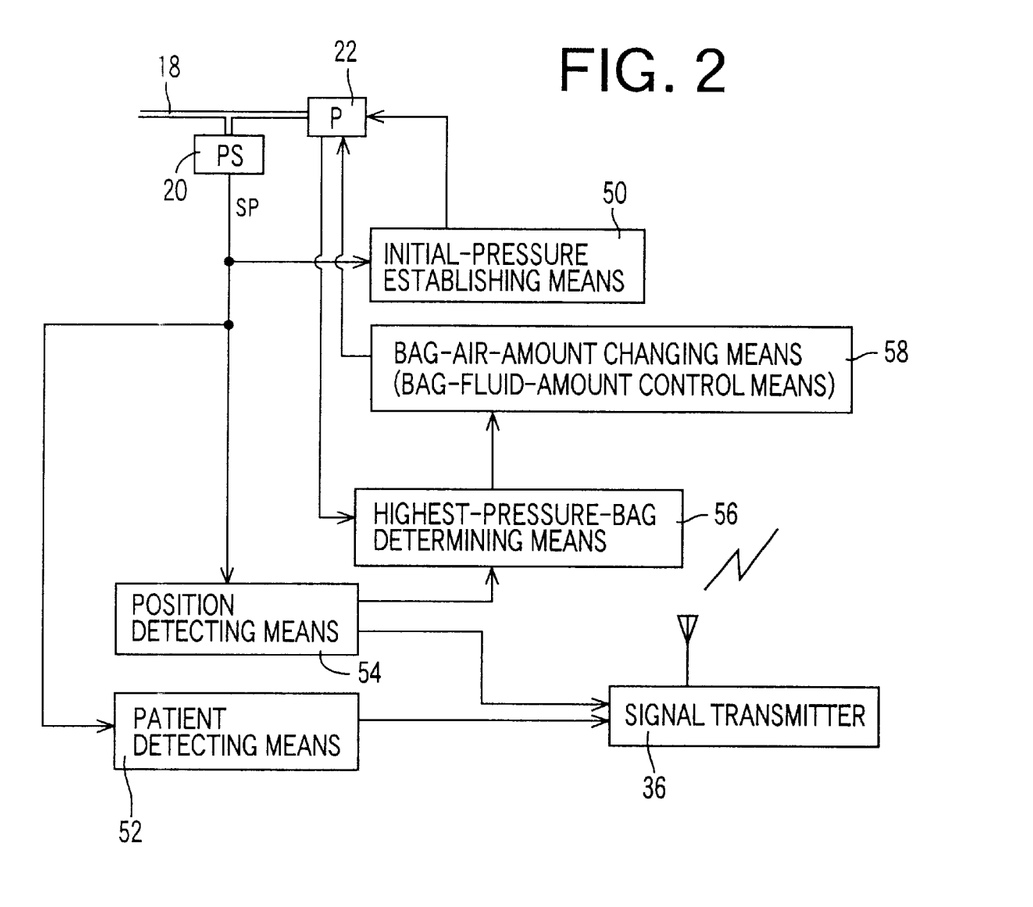
FIG. 2 is a block diagram for explaining essential functions of a control device of the apparatus of FIG. 1.

FIG. 2 is a block diagram for explaining essential functions of the control device 28. Though, in FIG. 2, only one pair of pressure sensor 20 and displacement pump 22 are shown, the control device 28 has an identical relationship with all pairs of pressure sensors 20 and displacement pumps 22. Therefore, the other pairs of pressure sensors 20 and displacement pumps 22 are omitted.

An initial-pressure establishing means 50 detects, from the electric signal SP supplied from each of the pressure sensors 20, an air pressure in a corresponding one of the pressure detecting bags 16, and operates a corresponding one of the displacement pumps 22 to change the air pressure of the one bag 16 to a prescribed initial pressure at which the one bag 16 is not fully inflated. The respective initial pressures of the pressure detecting bags 16 may be established when the patient is not present on the pressure detecting unit 14. Though each of the respective air pressures of the pressure detecting bags 16 can also be changed by a bag-air-amount changing means 58, as described later, the initial-pressure establishing means 50 periodically operates, at a prescribed patient-detecting period, one or more appropriate displacement pumps 22, each in a direction opposite to a direction in which the each pump 22 had been driven by the bag-air-amount changing means 58, by an amount equal to an amount by which the each pump 22 had been driven by the changing means 58, so that the amount of air currently present in its corresponding bag 16 is returned to the amount of air present in the bag 16 at the time when the initial pressure had been established therein. Hereinafter, a state in which the amount of air present in each bag 16 is equal to the amount of air present therein at the time of establishment of the initial pressure, will be referred to as the "initial-pressure state".

A patient detecting means 52 judges, in a state in which the respective amounts of air present in the five pressure detecting bags 16 are kept to their initial-pressure states by the initial-pressure establishing means 50, whether the patient is present on the bed 12, based on the respective electric signals SP supplied from the five pressure sensors 20. More specifically described, the patient detecting means 52 detects, in the state in which the respective amounts of air present in the bags 16 are kept to their initial-pressure states by the initial-pressure establishing means 50, the respective air pressures in the bags 16 based on the respective electric signals SP supplied from the pressure sensors 20, and judges, if at least one of the respective air pressures of the bags 16 is higher than a prescribed threshold value TH that is higher than the initial pressure, that the patient is present on the bed 12. On the other hand, if all the respective air pressures of the bags 16 are not higher than the prescribed threshold value TH, the patient detecting means 52 judges that the patient is not present on the bed 12. In the latter case, the patient detecting means 52 operates the signal transmitter 36 to transmit a signal representing an alarm that the patient is not present on the bed 12.

A position detecting means 54 identifies, in the state in which the respective amounts of air present in the pressure detecting bags 16 are kept to their initial-pressure states by the initial-pressure establishing means 50, one or more bags 16 whose air pressure or pressures is or are higher than the threshold value TH, based on the respective electric signals SP supplied from the five pressure sensors 20, and additionally determines, as a position where the patient is present, a position on the bag or bags 16 whose air pressure or pressures is or are higher than the threshold value TH. In addition, if the thus detected current position of the patient is located in one of prescribed widthwise opposite end portions of the bed 12, the position detecting means 54 judges that the patient is present at a dangerous position where the patient is likely to fall off the bed 12, and operates the signal transmitter 36 to transmit an alarm signal representing the situation.

A highest-pressure-bag determining means 56 determines, as a highest-pressure bag 16, one of the five pressure detecting bags 16 that most strongly presses the patient, based on the current position of the patient detected by the position detecting means 54, and the operation amount or amounts of one or more appropriate displacement pumps 22, from the initial-pressure state or states of the corresponding bag or bags 16, at the time before the bag or bags 16 is or are returned to the initial-pressure state or states by the initial-pressure establishing means 50 as described above. For example, the determining means 56 basically determines, as the highest-pressure bag 16, a middle one of the one or more bags 16 on which the current position of the patient has been determined by the position detecting means 54, because the middle bag 16, as seen in a widthwise direction of the patient, supports the greatest portion of the total weight of the patient who rests on the flat bed 12. However, if the current amount of air present in the middle bag 16 is smaller than that of either one of two adjacent bags 16 on opposite sides of the middle bag 16, that is, if the middle bag 16 is currently, less inflated than either one of the two adjacent bags 16, the determining means 56 determines, as the highest-pressure bag 16, one of the two adjacent bags 16 that exhibits the higher air pressure than that of the other adjacent bag 16 in the state in which the two adjacent bags 16 are kept to their initial-pressure states by the initial-pressure establishing means 50.

The bag-air-amount changing means 58, functioning as a bag-fluid-amount control means, periodically changes, at a prescribed pressure-changing period, respective amounts of air present in two or more appropriate pressure detecting bags 16, so that the highest-pressure-bag determining means 56 may determine a new highest-pressure bag 16 that is different from the prior highest-pressure bag 16. For example, the changing means 58 decreases the amount of air present in the prior highest-pressure bag 16 determined by the highest-pressure-bag determining means 56, down to the amount of air present therein at the time of establishment of the initial pressure, and increases the respective amounts of air present in two adjacent bags 16 on opposite sides of the prior highest-pressure bag 16, up to respective amounts more than by a prescribed amount than the amount of air present therein at the time of establishment of the initial pressure.

Figure 3:
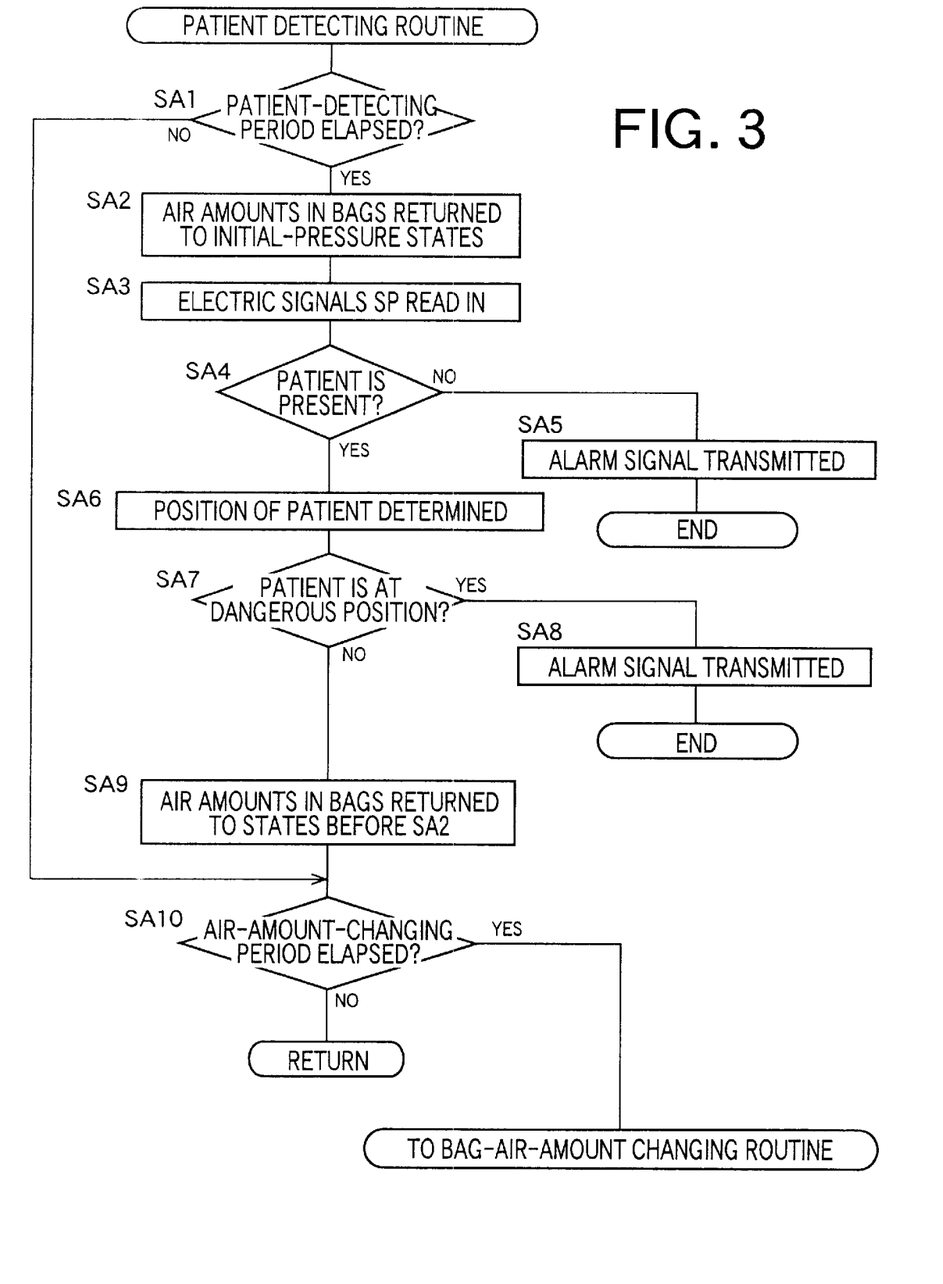
FIG. 3 is a flow chart representing a patient detecting routine according to which the control device of FIG. 2 operates.
Figure 4:
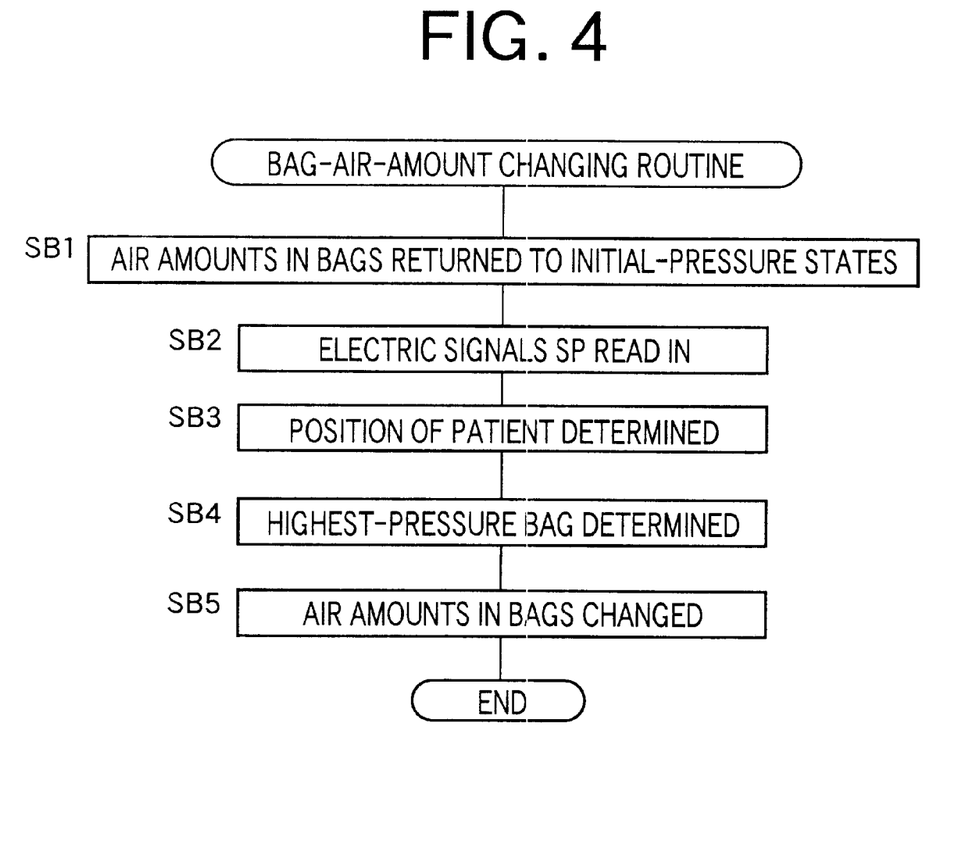
FIG. 4 is a flow chart representing a bag-air-amount changing routine according to which the control device of FIG. 2 operates.

FIGS. 3 and 4 show flow charts representing control routines according to which the control device 28 is operated. FIG. 3 shows a patient detecting routine; and FIG. 4 shows a bag-air-amount changing routine. Before the flow charts of FIGS. 3 and 4 are carried out, the respective amounts of air present in the five pressure detecting bags 16 are established or adjusted to their prescribed initial-pressure states, in the state in which the patient is not present on the pressure detecting unit 14 placed on the bed 12.

First, the patient detecting routine of FIG. 3 will be explained. In FIG. 3, first, the control device 28 carries out Steps SA1 to SA6 (hereinafter, the term "Step(s)" is omitted, if appropriate) corresponding to the patient detecting means 52. At SA1, the control device judges whether a prescribed patient-detecting period has elapsed after presence of the patient is last detected. The patient-detecting period is prescribed at a period (e.g., five minutes) that is sufficiently shorter than a prescribed air-amount-changing period, described later. If a negative judgment is made at SA1, the control goes to SA10, described later.

Meanwhile, if a positive judgment is made at SA1, the control goes to SA2 to operate appropriate displacement pumps 22, each by an amount equal to an amount by which the each pump 22 had been operated, at SB5 that will be described later, to increase the air pressure of the corresponding pressure detecting bag 16 from its initial-pressure state, but in a direction opposite to a direction in which the each pump 22 had been operated at SB5. Thus, the respective amounts of air present in the five pressure detecting bags 16 are returned to their initial-pressure states. Then, at SA3, the control device 28 reads in the electric signals SP supplied from the five pressure sensors 20.

In the state in which the respective amounts of air present in the five pressure detecting bags 16 are kept at their initial-pressure states, the control device can judge, if at least one of the respective air pressures in the five bags 16 is higher than the prescribed initial pressure, that the patient is present on the corresponding bag or bags 16. Therefore, at SA4, the control device judges, based on the respective pressure signals SP supplied from the pressure sensors 20, whether at least one of the respective air pressures of the five bags 16 is higher than a prescribed threshold pressure TH that is higher by a prescribed amount than the prescribed initial pressure, and thereby judges whether the patient is present on the bed 12. If a negative judgment is made at SA4, the control goes to SA5 to operate the signal transmitter 36 to transmit an alarm informing that the patient is not present.

On the other hand, if a positive judgment is made at SA4, that is, if it is judged that the patient is present on the bed 12, then the control goes to SA6 to SA9 corresponding to the position detecting means 54.

First, at SA6, the control device identifies, without exception, one or more pressure detecting bags 16 whose pressure or pressures represented by the electric signal or signals read in at SA3 is or are higher than the threshold value TH, and determines that the patient is present at a position on the thus identified bag or bags 16 in the widthwise direction of the bed 12.

Then, at SA7, the control device judges whether the position of the patient in the widthwise direction of the bed 12, determined at SA6, is a prescribed dangerous position. The dangerous position may be prescribed at a position on each of the opposite end bags 16 out of the five bags 16 as seen in the widthwise direction of the bed 12. If a positive judgment is made at SA7, that is, if the patient is present at the dangerous position where the patient is lightly to fall off the bed 12, the control device operates, at SA8, the signal transmitter 36 to transmit an alarm signal informing the situation.

On the other hand, if a negative judgment is made at SA7, the control goes to SA9 to operate each of the same displacement pumps 22 as those operated at SA2, in the direction opposite to the direction in which the each pump 22 had been operated at SA2, by the same amount as that by which the each pump 22 had been operated at SA2, so that the respective amounts of air present in the bags 16 corresponding to those pumps 22 are returned to their states before SA2 had been carried out. SA9 is followed by SA10 to judge whether a prescribed air-amount-changing period has elapsed after the bag-air-amount changing routine of FIG. 4, described later, had been last carried out. The air-amount-changing period is so prescribed as to prevent the patient from suffering bedsores that may result from continuous pressing of a specific portion of the patient, for example, the period is prescribed at several hours. If a negative judgment is made at SA10, the control goes back to SA1 and the following steps. Meanwhile, if a positive judgment is made at SA10, the control goes to the bag-air-amount changing routine of FIG. 4.

Next, the bag-air-amount changing routine of FIG. 4 will be explained. In FIG. 4, first, the control device carries out SB1 to SB corresponding to the highest-pressure-bag determining means 56. SB1 and SB2 are identical with SA2 and SA3 of FIG. 3, that is, the respective amounts of air in the bags 16 are returned to their initial-pressure states and, in this state, the control device reads in the respective electric signals SP supplied from the pressure sensors 20. SB3 is identical with SA6, that is, the control device identifies, based on the respective pressures in the bags 16, represented by the electric signals SP read in at SB2, one or more bags 16 on which the patient is present.

Subsequently, at SB4, the control device determines a highest-pressure bag in the following manner: If the amount of air present in a widthwise middle one of the one or more bags 16 identified at SB3 is equal to, or more than, the respective amounts of air present in two adjacent bags 16 on opposite sides of the middle bag 16, the control device determines the middle bag 16 as the highest-pressure bag. The respective air amounts of the middle bag 16 and the two adjacent bags 16, compared with each other, are the air amounts thereof in their states before those bags 16 had been returned to their initial-pressure states at SB1. On the other hand, if the amount of air present in the middle bag 16 is less than the respective amounts of air present in the two adjacent bags 16, the control device determines, as the highest-pressure bag, one of the two adjacent bags 16 that shows the higher air pressure, represented by the corresponding electric signal SP read in at SB2, than that shown by the other adjacent bag 16.

Then, the control proceeds with SB5 corresponding to the bag-air-amount changing means 58. At SB5, the control device operates for changing the amount of air present in the highest-pressure bag determined at SB4, to the amount of air present therein at the time of establishment of the initial-pressure state, and increasing, by a prescribed amount, each of the respective amounts of air present in two adjacent bags 16 on opposite sides of the highest-pressure bag. Thus, the highest-pressure bag is deflated, and the two adjacent bags 16 on the opposite sides of the highest-pressure bag are inflated, so that a different bag 16 than the prior highest-pressure bag may support the greatest proportion of a body weight of the patient.

As is apparent from the foregoing description of the present invention, the plurality of pressure detecting bags 16 are provided in the widthwise direction of the bed 12, and produces the respective pressure signals. Thus, the plurality of pressure signals are obtained in the widthwise direction of the bed 12. Since the position detecting means 54 (SA6 to SA9) detects, based on those pressure signals, the position of the patient in the widthwise direction of the bed 12, the present apparatus 10 can judge whether the position of the patient is a dangerous position where the patient is likely to fall of the bed 12.

In addition, in the present embodiment, the bag-air-amount changing means 58 (SB5) changes the respective amounts of air present in the pressure detecting bags 16, so that a different bag 16 than the prior bag 16 may support the greatest proportion of the body weight of the patient. Thus, the present apparatus 10 can effectively prevent the patient from suffering bedsores.

While the present invention has been described in its preferred embodiment, the present invention may be otherwise embodied.

Figure 5:
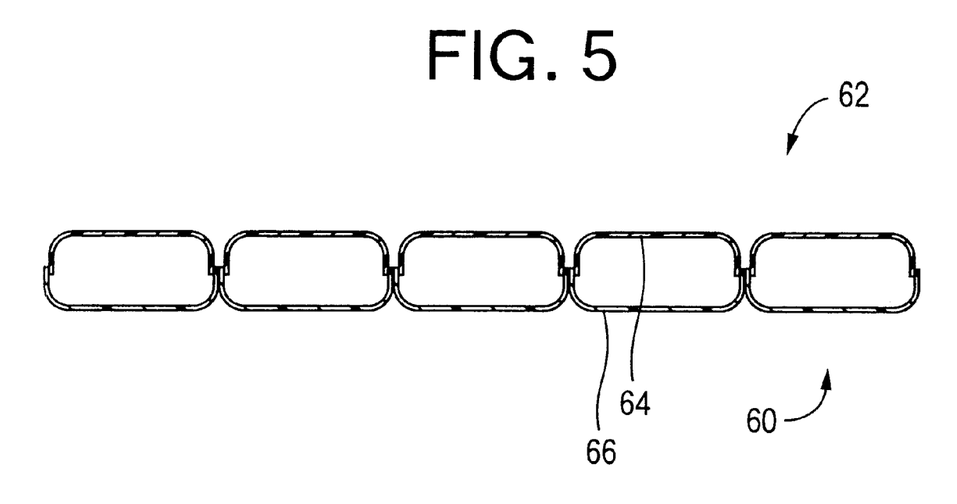
FIG. 5 is a transverse cross section of a pressure detecting unit which is employed in another patient detecting apparatus as a second embodiment of the present invention and which includes a plurality of pressure detecting bags an upper half portion of each of which is formed of a porous resin sheet.

For example, in the illustrated embodiment, each of the pressure detecting bags 16 is formed of the air-tight sheet. However, an upper portion, or an entirety, of each of the bags 16 may be formed of a porous sheet. FIG. 5 shows a transverse cross section of a pressure detecting unit 62 including a plurality of pressure detecting bags 60 an upper portion 64 of each of which is formed of a porous resin sheet. As shown in FIG. 5, each bag 60 includes the upper portion 64 that contacts the patient, and a lower portion 66 that contacts the bed 12. The upper and lower portions 64, 66 are connected to each other by an adhesive or high-frequency welding to provide the each bag 60. The lower portion 66 is formed of a flexible synthetic-resin sheet, such as soft vinyl-chloride sheet or nylon sheet. The upper portion 64 is formed of a porous resin sheet having a number of fine pores having respective diameters of from several microns to several hundreds of microns, and allows air to permeate or leak from inside the each bag 60 to an outside space. The porous resin sheet may be a polyethylene sheet. When each bag 16 having the above-described structure is supplied with pressurized air, the air leaks through the fine pores of the each bag 16 to the side of the patient. Thus, the present pressure detecting unit 62 can prevent an air having a high humidity from remaining between the unit 62 and the patient.

In the illustrated embodiment, each of the pressure detecting bags 16 is filled with air. However, each bag 16 may be filled with a liquid such as water in place of air.

In the illustrated embodiment, the pressure detecting bags 16 each as a pressure detecting device detects an air pressure therein and thereby detects the patient. However, the pressure detecting devices may be provided by a number of pressure switches which are adapted to be provided in a mat placed on the bed 12 and produce respective detection signals, so that the control device 28 can detect the patient based on the detection signals supplied from the switches.

In the illustrated embodiment, the pressure detecting bags 16 are associated with the respective displacement pumps 22. However, the five tubes 18a, 18b, 18c, 18d, 18e may be connected to a single displacement pump 22 via an automatic switching valve. In the latter case, the automatic switching valve sequentially connects, at a prescribed switching period, the pump 22 to each of the tubes 18. In addition, in the latter case, one of the tubes 18 may be connected to an inflatable cuff and a pressure sensor for use in a blood-pressure measurement. In this case, the pump 22 also functions as a pump for use in the blood-pressure measurement.

It is to be understood that the present invention may be embodied with other changes, improvements, and modifications that may occur to a person skilled in the art without departing from the spirit and scope of the invention defined in the appended claims.

What is claimed is:

1. An apparatus for detecting a patient, comprising:

a plurality of pressure detecting devices which are adapted to be placed on a bed such that the pressure detecting devices are arranged in a widthwise direction of the bed, and which detect respective pressures and produce respective pressure signals representing the detected pressures; and a position detecting means for detecting, based on the pressure signals supplied from the pressure detecting devices, a position, in the widthwise direction of the bed, where the patient is present; wherein the pressure detecting devices comprise respective bags each of which is filled with a fluid, and wherein the apparatus further comprises a fluid-amount control means for controlling an amount of the fluid present in each of the respective bags of the pressure detecting devices, the fluid-amount control means comprising changing means for identifying a first bag of the respective bags that supports a greatest portion of a total weight of the patient, and changing the respective amounts of the fluid present in the respective bags of two or more pressure detecting devices so that a second bag of the respective bags that is different from the first bag supports a greatest portion of the total weight of the patient.

2. An apparatus according to claim 1, wherein the pressure detecting devices comprise respective bags each of which is filled with an air and includes a contact portion that is adapted to contact the patient and is formed of a porous sheet, the porous sheet allowing the air to permeate therethrough into an outside space, and wherein the apparatus further comprises an air pump which supplies the air to said each of the respective bags.

* * * * *